United States Patent [19]

Weber

[11] Patent Number: 4,576,777

[45] Date of Patent: Mar. 18, 1986

[54] ENERGY DETECTION METHOD AND APPARATUS

[76] Inventor: Joseph Weber, 9 W. Melrose St., Chevy Chase, Md. 20015

[21] Appl. No.: 295,002

[22] Filed: Aug. 21, 1981

Related U.S. Application Data

[63] Continuation-in-part of Ser. No. 118,184, Feb. 1, 1980, abandoned, which is a continuation-in-part of Ser. No. 833,678, Sep. 15, 1977, abandoned, which is a continuation-in-part of Ser. No. 710,295, Jul. 30, 1976, abandoned.

[51] Int. Cl.$^4$ ............................................. G21C 17/00
[52] U.S. Cl. .................................... 376/153; 250/251; 250/336.1
[58] Field of Search ................ 455/620; 324/304, 313, 324/316, 307; 250/336.1, 251, 390–392; 376/153; 73/382

[56] References Cited

U.S. PATENT DOCUMENTS

| | | | |
|---|---|---|---|
| 2,929,932 | 3/1960 | Bouricius et al. | 250/392 |
| 3,067,365 | 12/1962 | Sailor et al. | 250/390 |
| 3,424,006 | 1/1969 | Dicke et al. | 73/382 |
| 3,554,033 | 1/1971 | Weber | 73/382 |
| 3,722,284 | 3/1973 | Weber et al. | 73/382 |
| 3,722,285 | 3/1973 | Weber | 73/382 |
| 3,722,286 | 3/1973 | Weber | 73/382 |
| 3,722,287 | 3/1973 | Weber | 73/382 |
| 3,722,288 | 3/1973 | Weber | 73/382 |
| 3,722,289 | 3/1973 | Weber | 73/382 |
| 3,722,290 | 3/1973 | Weber et al. | 73/382 |
| 3,970,936 | 7/1976 | Arnold | 455/620 |
| 4,205,268 | 5/1980 | Eerkens | 455/620 |

OTHER PUBLICATIONS

Kozponti Fizikai Kutato Intezet, Budapest, pp. 411–421, Szalay.
Neutrino Dynamics in Stellar Collapse, Bludman, pp. 329–362, 6/12/75.
Phys. Rev. D., vol. 27, No. 6 (3/15/83) Langacker et al., pp. 1228–1242.
Astom, S. Astrophys. 37, 135–137 (1974) Opher (I).
Astom, S. Astrophys. 46, 253–255 (1976) Opher (II).
Phys. Rev. D., vol. 8, No. 5 (9/73) pp. 1343–1357, Bjorken et al.
Astrophysical Journal, 201, 467–488, (10/75) Tubbs et al.

(List continued on next page.)

Primary Examiner—Sal Cangialosi
Attorney, Agent, or Firm—Lowe, King, Price & Becker

[57] ABSTRACT

An energy beam, particularly a neutrino beam or an optical radiation beam, is detected by irradiating a material with the beam in the presence of electromagnetic fields. The material is such that the beam is coherently scattered thereby, and the coherent scattering of the beam causes coherent stimulated emission of radiant energy fields in the material. Electric or magnetic fields adjust the scatterer energy levels so that energy and momentum are conserved overall, and for detection. The neutrino beam causes derivation of RF photons which are detected by a radio receiver. Alternatively, the neutrino beam irradiates a bulk material having nuclei with non-zero spin and non-zero magnetic moments and with sufficient stiffness to recoil as a single entity after absorbing momentum from each neutrino in the beam. Optical radiation photons irradiate a transparent bulk material having nuclei with non-zero spin and non-zero magnetic moments; the nuclei have sufficient stiffness to recoil as a single entity after absorbing momentum from each photon. An applied D.C. magnetic field produces a significantly large number of aligned magnetic moments in the material for photon scattering. An optical beam is also detected by irradiating a capacitor having a transparent electrode that is biased to produce free electrons at an interface between the electrode and a dielectric. The free electrons scatter the optical radiation to produce coherent RF energy that is detected by a radio receiver. An optical beam is also detected by irradiating a crystal having magnetic dipoles aligned by a magnetic field. A coherent interaction between the dipoles and beam occurs to change the dipole spin state that is detected by a nuclear magnetic resonance detector.

69 Claims, 6 Drawing Figures

OTHER PUBLICATIONS

Kozponti Fizikai Kutato Intezet, Budapest (Hungary) pp. 363-382 (1975) Chechetkin et al.

Physical Review D., vol. 9, No. 5 (Mar. 1, 1974) Freedman, pp. 1389-1392 "Coherent Effects of a Weak Neutral Current".

Phy. Rev. Letter, vol. 32, No. 15 (Apr. 15, 1974) Wilson, pp. 849-852 "Coherent Neutrino Scattering and Stetlar Collapse".

New Method in Elementary Particle Detection, Weber (2/83).

J. Geo. Res. (vol. 71, No. 24) (12/15/66) Weber et al., pp. 6005-6009.

Barish, B. C., "Experiments with Neutrino Beams", *Scientific American*, (8/73) pp. 30-38.

"Evidence for Discovery of Gravitational Radiation"; J. Weber; *Physical Review Letters;* vol. 22, No. 24; Jun. 16, 1969; pp. 1320-1324.

"Gravitational Radiation Experiments"; J. Weber; reprint from *Physical Review Letters;* vol. 24, No. 6; Feb. 9, 1970a; pp. 276-279.

"Anisotropy and Polarization in the Gravitational-Radiation Experiments"; J. Weber; *Physical Review Letters,* vol. 25, No. 3; Jul. 20, 1970b; pp. 180-184.

"Gravitational Radiation Experiments"; J. Weber; *Relativity and Gravitation,* Paper No. 35; Eds. C. Kuper and A. Peros., Gordon and Breach Science Publishers; London; pp. 309-322.

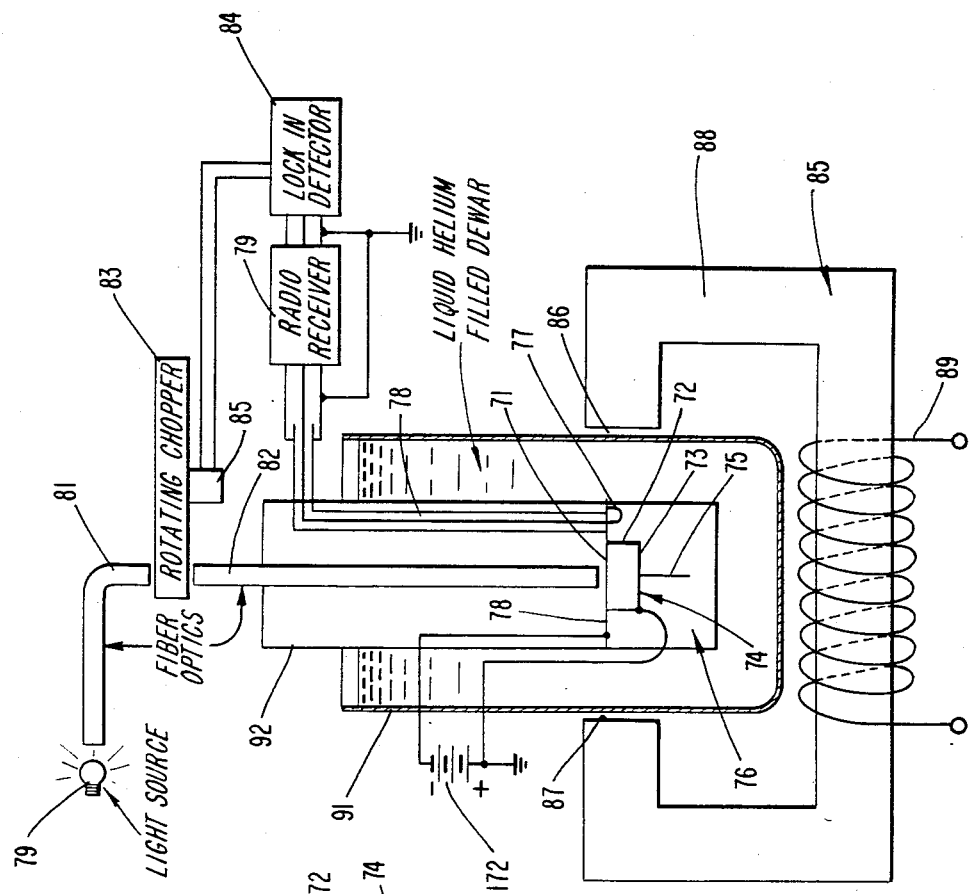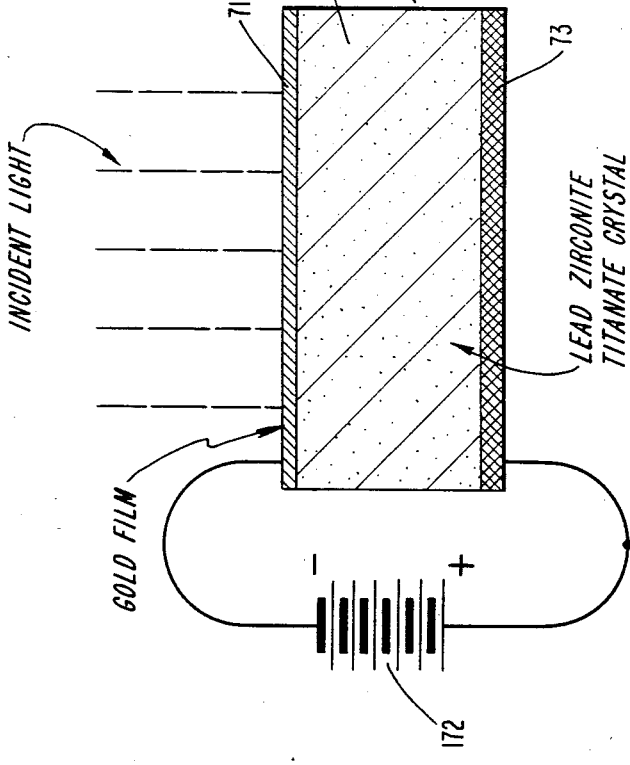

ENERGY DETECTION METHOD AND APPARATUS

RELATION TO CO-PENDING APPLICATION

The present application is a continuation-in-part of my abandoned co-pending application Ser. No. 118,184, filed Feb. 1, 1980; which is a continuation-in-part of abandoned Ser. No. 833,678, filed Sept. 15, 1977; which in turn is a continuation-in-part of now abandoned Ser. No. 710,295, filed July 30, 1976.

FIELD OF THE INVENTION

The present invention relates generally to detecting energy carrying beams by coherent effects, and more particularly, to methods and apparatus for detecting beams that irradiate a material to emission of coherent radiant energy from the material, or to induce observable changes in the quantum states of scatterers within the material.

BACKGROUND OF THE INVENTION

Many different detectors for wave and particle energy have been devised. However, there are very few, if any, practical detectors presently being used to indicate the occurrence of the relatively high energy neutrino beams, or electromagnetic energy beams in the far infrared, between 1 mm and 100 microns. I have discovered that it is possible to detect several forms of energy over an extremely wide spectrum, at least from the far infrared to the million electron volt neutrino region, by relying upon coherent scattering effects of subatomic particles of a material irradiated by the beam. Prior to discussing the techniques and apparatus for detecting electromagnetic energy over this extremely wide spectrum, consideration will be given to background material relating to neutrinos.

According to the theory of radioactive beta decay, a neutron causes a proton, negative electron (or beta particle) and anti-neutrino to be derived. Anti-neutrinos are the anti-particles of neutrinos and are produced when a neutron undergoes decay to an electron and a proton. For the purposes of the present disclosure, neutrinos and antineutrinos are generally classified as neutrinos, unless otherwise indicated. Neutrinos are uncharged particles having a rest mass less than 0.05% of the rest mass of an electron, and an intrinsic spin angular momentum of $\hbar/2$, where $\hbar = h/2\pi$ and $h =$ Planck's constant $= 6.625 \times 10^{-34}$ joule sec. The interaction of neutrinos with matter is so weak that neutrinos penetrate all matter practically unhindered. Direct evidence for the existence of neutrinos has been previously obtained only under great difficulties, either by observing a reaction inverse to the beta decay or by high energy experiments. The difficulties involved in detecting the existence of neutrinos are so great that approximately 25 years elapsed from the theoretical prediction of their existence in 1930, to experimental proof of their existence in 1953.

Despite the difficulties involved in detecting the existence of neutrinos, it is desirable to detect the presence thereof. In particular, properties of a nuclear reactor can be determined by monitoring neutrinos emitted from the reactor. Also, it is possible to transmit information by modulating a neutrino beam or flux.

BRIEF DESCRIPTION OF THE INVENTION AND THEORETICAL DISCUSSION

It is known that neutrinos, antineutrinos and photons of optical and certain radio frequency waves are scattered by subatomic particles, e.g., electrons or nuclei of atoms, when they impinge on a material.

The scattering is described quantitatively by the concept of cross section, defined by the statement:

Cross section =

$$\frac{\text{Number of particles scattered per second in a certain range of some variable}}{\text{Number of incident particles per second per unit area}}$$

Usually a differential range of solid angle is implied and the term differential scattering cross section employed. The total cross section is then the integral over all scattering angles.

For certain kinds of scattering by the large number of scatterers in bulk matter, there are no significant interference effects. In other cases there are sharp maxima and minima resulting from interference effects of different scatterers.

Large random phase shifts which are sometimes associated with each scatterer contribution, may prevent significant constructive interference. A large random phase shift may occur if the final quantum state of each scatterer is substantially different from the initial quantum state. For instance, in the scattering of X rays and neutrons the spin of a single scatterer may change. This makes it possible to identify an individual particle as the object which scattered the incident beam. The scattering is said to be incoherent.

When large random phase shifts do not occur, large interference effects are observed. These interference effects result in large intensity interference peaks which provide the basis for coherent X rays and neutron scattering analyses of the structure of materials.

While no large random phase shifts occur in coherent scattering, there are non-random phase shifts, at each scatterer. The non-random phase shifts are proportional to the vector difference of incident and scattered particle momenta. These non-random phase shifts produce strong very narrow intensity peaks, by constructive interference. The peak intensity is proportional to the square of the total number of scatterers. The peaks are however very narrow, and the integration over angles gives a very small total cross section. This invention is concerned with means for enormously increasing the total cross section.

It is proposed here that an additional phase shift be introduced at each scatterer, which additional phase shift is due to the recoil momentum of all scatterers recoiling as a single entity. This phase shift reduces the non-random phase shift associated with the difference of incident particle momenta before and after scattering. The addition to incident particle and common scatterer momenta results in enormously widening the interference peaks. A large increase in total cross section and in detection sensitivity may result.

The additional phase shift can be obtained from a recoil momentum which is identical for all scatterers. For this reason very great stiffness may be required, since the interaction with one scatterer must cause all other scatterers to recoil. The recoil of all the other scatterers must occur in such a way that no observations can distinguish a particular scatterer as the interacting object. A measure of the required stiffness is the square of the recoil momentum divided by twice the mass of the scatterer. This recoil energy must be very small compared with the energy which binds the scatterer to a particular site.

The additional non-random phase shift does not occur if the initial quantum states of the scatterers correspond to precisely known momenta, and may occur for initial quantum states for which positions are quite precisely known.

Finally, the system must be so arranged that energy and momentum can be conserved for a significant volume of phase space. To obtain a large cross section, the entire ensemble of scatterers must exchange energy momentum with incident particles. This must occur in such a way that no single scatterer can be subsequently identified as having exchanged a different energy momentum from the other scatterers.

In accordance with the invention, neutrinos or photons are detected by causing them to irradiate a material in such a manner as to cause the material to scatter coherently. The material is located in a cavity that provides means to efficiently couple coherent energy resulting from the coherent scattering to an output device. A pickup for the coherent energy located in the mass material transduces the coherent energy into a coherent wave that is supplied to an amplifier tuned to the relevant frequencies of the cavity. The material is shielded from ambient effects of the coherent wave energy so that such energy originating outside of the material is decoupled from the material and the pickup is responsive solely to the energy induced in the material in response to the neutrinos or photons of the beam to be detected.

In accordance with one of the embodiments for detecting neutrinos the material is a solid including particles that are stimulated to an unstable state in response to the neutrino radiation. As the particles return to a stable state, photons may be emitted to produce electromagnetic coherent energy, or the coherent particle response is detected by the fields of the particles. The material is located in an electrically conducting chamber which functions as an electrical shield and is pervious to neutrinos. The chamber has dimensions enabling it to be responsive to the coherent energy induced in the material by the neutrinos. A coherent electromagnetic field may be derived in the cavity; the frequency of the field is determined by the division of incident neutrino energy into a part which is scattered as a neutrino, a part which is electrical energy and a part which is absorbed as heat. The electromagnetic field is transduced into an electrical voltage by an electromagnetic pickup, such as a loop or probe, located in the shielded resonant cavity so that the pickup is unresponsive to ambient electromagnetic fields outside of the material. The transduced voltage is coupled to an RF amplifier tuned to the frequencies of the coherent electromagnetic energy.

In one embodiment, the irradiated material has a random particle spin orientation, whereby photons emitted in the material in response to neutrino irradiation have an electric field component in a direction preferentially normal to the direction of neutrino propagation through the material.

In a second embodiment, having a higher efficiency than the first embodiment, the irradiated material is a material including particles with magnetic moments in which particle spins are preferentially aligned along some direction. The particle spins are preferentially aligned by applying a polarizing field to the material. Greater efficiency occurs with the second embodiment because there are fewer steps governed by probability.

The neutrino interactions during scattering modify the spin quantum states of the scatterers. These scatterer spin state transitions, i.e. the transitions of the particles in spinning from the state to which they are initially excited by the neutrinos to the final spin state, are affected by the neutrino energy without random effects on the phase of the field contributed by each scatterer. Detection sensitivity can be further improved by operating the device at cryogenic temperatures where background fields and noise are much smaller than at room temperature.

In a preferred embodiment, a magnetic field is alternately supplied to and removed from the material containing magnetic particles to modulate the separation between the initial and final spin states, thereby modulating the interaction of the neutrinos and the particles.

The alternate sequences of coherent energy and noise are coupled through a wideband radio receiver to a detector that is synchronized with the alternate application of the magnetic field to the material.

The principles of the invention can be extended to the situation wherein the neutrinos irradiate a solid material in which phonons, rather than photons, are emitted to produce coherent acoustic radiant energy. The solid material must be a good acoustic transmitter, having low acoustic losses. Examples of suitable materials are aluminum and quartz. The acoustic transmitter is located in an acoustic chamber that is acoustically isolated, i.e., shielded, from its ambient conditions. An acoustic-electrical transducer, such as a piezoelectric crystal, is located in the chamber to derive an electric wave having a frequency determined by the division of incident neutrino energy into a part which is scattered as a neutrino, a part which is emitted as a phonon and a part which is absorbed as heat.

In accordance with still a further embodiment of the invention, neutrinos are detected with a bulk material having nuclei with non-zero spin and non-zero magnetic moments. The material has sufficient stiffness to recoil as a single entity after absorbing momentum from each neutrino in the beam. Exemplary of such materials are crystals of sapphire or silicon, which respectively include the isotopes 27Al and 29Si that exhibit nuclear magnetic resonant properties when excited with appropriate magnetic fields. While the material is irradiated by the neutrinos, a magnetic field is applied to it. The magnetic field causes the nuclei to normally precess about the longitudinal axis of the magnetic field at a predetermined angle. The neutrino may cause a shift in the precessing angle, or may modify the quantum states of the spins by altering correlations set up by applied electromagnetic fields, which changes are detected by utilizing a nuclear magnetic resonance detection apparatus. To enable the nuclear magnetic resonance fields to be detected, the magnetic field intensity of the field exciting the material is substantially equal to:

$$H = \frac{E_\nu}{4\mu_m \beta \sqrt{2N}}$$

where:

$E_\nu$ = the energy of neutrinos in the beam;

$\mu_m$ = the scattering nuclear magnetic moment of the material;

$\beta^2$ = the fraction of nuclei of the material with moments parallel to the direction of the magnetic field;

N = the total number of neutrino scatterers of the material.

The material is considered to be a stiff crystal that has the proper recoil properties if the product of Boltzmann's constant ($1.38 \times 10^{-23}$ joules per degree centigrade) and the Debye temperature of the crystal is much greater than (at least an order of magnitude) $p^2/2m$, where p = the momentum of an irradiating neutrino ($p = E_\nu/c$), $E_\nu$ = the energy of the neutrino; c = the speed of light; and m = the mass of each scatterer.

Because special coherent principles are utilized in the present invention, the detection efficiency and scattering cross section of particles irradiated by the neutrinos are proportional to the square of the number of particles that absorb or scatter the neutrinos, in contrast to the prior art wherein detection efficiency is either proportional to the total number of atoms or other relevant particles which act as neutrino absorbers or scatterers, or proportional to the square of the number of scatterers multiplied by a very small quantity.

To detect beams of optical energy, either coherent or incoherent beams, the beam irradiates transparent stiff material containing nuclei with non-zero spin and non-zero magnetic moments. An applied D.C. magnetic field creates a significantly large number of aligned magnetic moments which act as coherent scatterers. Detection is by observation of a change in spin quantum states of the scatterers. In another embodiment the beam irradiates a material containing charged particles that coherently scatter photons of the optical energy beam. In response to the coherent scattering of the photons, the scatterers cause the derivation of a coherent ensemble of photons having a frequency much lower than the frequency of the optical energy.

In the embodiment in which the nuclei contain non-zero spin and magnetic moments while the material is irradiated by the optical beam, a magnetic field is applied to the material to cause the scatterers to normally precess about the magnetic field at a predetermined angle. The beam causes a shift in the quantum states of the scatterers. The shift in the precessing angle of the scatterers causes the lower frequency photons and a corresponding electromagnetic field to be derived. Typically, the much lower frequency is a microwave frequency and a resonator is provided for coupling the resulting microwave, electromagnetic field to amplifiers via a suitable transmission medium. The resonator includes an aperture for enabling the optical beam to impinge on a conducting button. However, the aperture has a geometry, i.e., shape and dimensions, such that it is beyond cut-off for the RF field, whereby the RF field cannot escape from the resonator through the aperture. Because the invention is particularly adapted to be utilized in a wavelength region where IR detectors have not previously been generally successful, from 1 mm to 100 microns, the intensity of the magnetic field applied to the button to cause the coherent derivation of photons may be small, less than the ambient magnetic field of the earth. Therefore, it may be necessary to shield the apparatus from the magnetic field of the earth, a result achieved by utilizing a superconducting shield.

The theoretical analysis included in my enclosed report entitled "Scattering By Very Tightly Bound Ensembles" shows that constructive interference, and therefore large cross section coherent scattering, occurs in the present invention in response to irradiation of a suitable material by an electromagnetic beam having quanta of energy that interact appropriately with the subatomic particles of the material.

In still another embodiment that apparently does not rely upon coherent scattering, a material having magnetic dipoles is subjected simultaneously to an energy beam, preferably of optical radiation, and a magnetic field that aligns the dipoles. A coherent interaction between the aligned dipoles and the beam occurs to cause a magnetic dipole spin state change that is detected, preferably by a nuclear magnetic resonant detector.

It is accordingly an object of the present invention to provide a new and improved method of and apparatus for detecting beam energy, and particularly to detecting beams containing forms of energy that cause coherent scattering of subatomic particles of a material.

An additional object of the invention is to provide a method of and apparatus for detecting neutrinos by causing the neutrinos to irradiate a material in such a manner that stimulated emission of coherent radiant energy occurs in the material.

An additional object of the invention is to provide a new and improved method of and apparatus for detecting an electromagnetic energy beam by causing photons in the beam to irradiate a material in such a manner that stimulated emission of coherent radiant energy occurs in the material.

A further object of the invention is to provide a method of and apparatus for detecting neutrinos or optical energy by responding to coherent electromagnetic radiant energy that is stimulated in a material in response to the material being irradiated by the neutrinos or photons of the optical energy.

Yet another object of the invention is to provide a method of and apparatus for detecting neutrinos or optical energy beams in response to the derivation of coherent forms of energy in the material in response to coherent scattering by subatomic particles of the material resulting from irradiating by the neutrinos or photons in the optical energy beams.

Another object of the invention is to provide a method of and apparatus for detecting beams of neutrinos or optical energy in response to changes in the spin states of particles that are in a material having particles with magnetic moments which are irradiated by the neutrinos.

Another object of the invention is to provide a new method of and apparatus for determining the direction of propagation of neutrinos, i.e., a neutrino telescope.

The propagation direction of neutrinos can be detected because available stiff materials are anisotropic with different stiffness in different directions. The total cross section therefore varies in different directions. The detection system can therefore be arranged so that the device functions as a telescope.

The above and still further objects, features and advantages of the present invention will become apparent upon consideration of the following detailed description of several specific embodiments thereof, especially when taken in conjunction with the accompanying drawing.

BRIEF DESCRIPTION OF THE DRAWING

FIGS. 3 and 4 are schematic diagrams of two optical energy detector embodiments wherein free electrons are coherently scattered by photons of an optical energy beam;

FIG. 5 is a more detailed diagram of the detector of FIG. 4; and

DETAILED DESCRIPTION OF THE DRAWING

Figure 1:
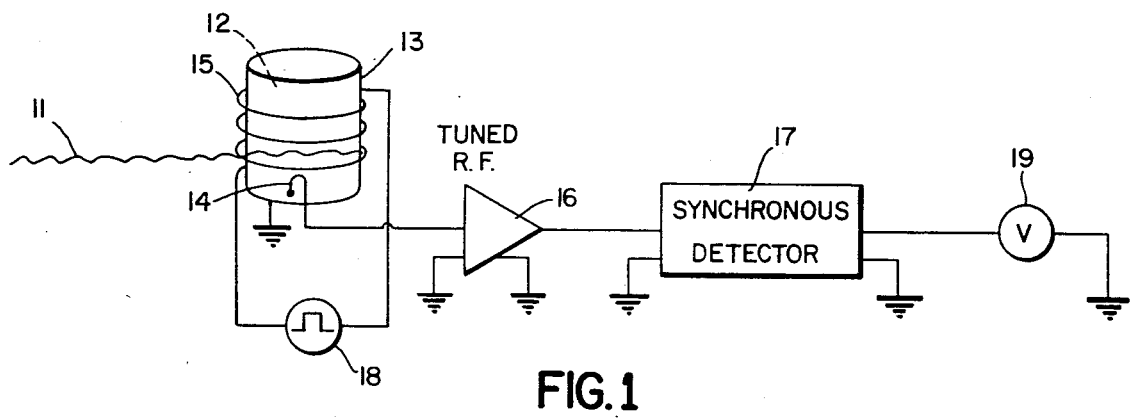
FIG. 1 is a block diagram of an apparatus for detecting neutrinos in response to photons being coherently derived in a material in response to neutrino irradiation.

Reference is now made to FIG. 1 wherein there is illustrated a beam 11 of neutrinos which is derived from a suitable source, typically a nuclear reactor. Neutrino beam 11 may be modulated by inserting rods into the reactor, whereby the beam carries information.

Beam 11 moves along a propagation path (along the z axis of a Cartesian coordinate system) so that it impinges on dielectric 12 that is maintained in an electrically shielded container 13 that forms an electric circuit for modes of the electromagnetic field. Dielectric material 12 has a very low electric loss factor; from certain experiments it appears that sapphire, lithium niobate, and lithium fluoride are appropriate materials. In one preferred embodiment, material 12 is a paramagnetic, dielectric material in which the neutrino beam 11 causes atomic nuclei to undergo spin changes. Typically, container 13 has the shape of a cylinder and is formed of sheet aluminum having thickness on the order of one-half inch so that it functions as an optimum electric shield, while being pervious to neutrinos and to an external magnetic field. Cavity 33 need not be located in the nuclear reactor, since neutrinos from the source within the reactor are capable of penetrating through the walls of the reactor.

There is located within container 13 an electromagnetic pick-up, in the form of loop 14; the pick-up may also be a probe. Hence, the pick-up is not affected by external, ambient electromagnetic fields, but is responsive only to electromagnetic fields derived within the container.

The electromagnetic field derived within container 13 occurs in response to the interaction of neutrinos 11 and particles or nuclei in material 12 which produces stimulated emission of coherent fields within container 13, i.e., the neutrinos pump the particles or nuclei to an unstable state and a coherent field is produced as the particles return to a stable, ground state. The frequency of the coherent field derived in container 13 is a function of the division of the neutrino energy into a scattered neutrino, the electromagnetic field and heating of the cavity material. The RF electromagnetic field stimulated in material 12 may have polarizations such that electromagnetic modes are induced with propagation directions primarily normal to the direction of propagation of the neutrinos.

In the illustrated embodiment, material 12 has an internal magnetic field polarization and is formed of a paramagnetic material that can be excited to a change in a mixture of two particle spin states in response to the neutrino beam. The internal polarization is established by applying an external magnetic field to the material by feeding a DC current through a coil that is wrapped around container 13. Neutrinos interact with the magnetic moment particles to change the particle spin state. The spin states are separated by a desired amount by adjusting the magnitude of the magnetic field applied by coil 15 to the magnetic moment particles of material 12.

Electromagnetic wave to electric wave transducer 14 derives electric waves having frequencies equal to the frequencies of the electromagnetic waves derived in material 12. The electric wave transduced by loop 14 is applied to input terminals of relatively wide band RF amplifier 16 that is tuned to the frequencies of the fields derived by loop 14. To minimize noise, amplifier 16 is of high quality and low noise. Efficient detection of the output of amplifier 16 can be derived by applying the amplifier RF output wave to a synchronous detector 17.

In the illustrated embodiment, wherein material 12 is a paramagnetic substance, current having a DC component plus a square wave variation is coupled to coil 15 in response to the output of low frequency, square wave source 18; typically, source 18 has a frequency on the order of 25 Hertz. Thereby, amplifier 16 derives an output that is modulated at 25 Hertz, wherein alternate 25 Hertz half-cycles of the amplifier output contain a coherent RF carrier, and the remaining half-cycles contain a different amount of RF energy. The two kinds of half-cycles are separated in synchronous detector 17 that is driven by the output of source 18. Detector 17 thereby identifies the signal and derives a DC output related to the amplitude of the coherent field derived by transducer 14 during the half-cycles while current is applied to coil 15. The DC output of synchronous detector 17 is derived from an indicator 19, which may be a DC voltmeter.

In practice, the neutrinos may have an energy in excess of $10^6$ electron volts. Material 12 is selected so that a good compromise is achieved between the greater efficiency effects of high frequency coherent electromagnetic fields and the noise problems inherent with certain high frequency operations.

EXPERIMENTS

The theory already presented suggests that coherent scattering might be observed, with large total cross sections (i.e. materials having a macroscopically large cross section interacting with an energy beam) for the scattering processes; in this connection see Appendix D of my enclosed report "Scattering By Very Tightly Bound Ensembles", wherein a first scattering case is electron scattering by a neutrino to cause the neutrino to change its energy momentum and a change in neutrino direction. The scattered neutrino interacts with an electromagnetic field and again changes the direction of the neutrino. In a second case, a similar process occurs in the opposite order so that the neutrino direction is initially changed by the electromagnetic field and then by the electron, to produce photons. In these scattering processes a neutrino is scattered by an electron and a low frequency photon is emitted.

One series of experiments was carried out by employing a large tank of demineralized water, four feet in diameter and 4 feet long. A second series employed manganese nitrate in a chamber 20 inches in diameter and 20 inches long. The reactor at the National Bureau of Standards in Gaithersburg, Md. was employed. The reactor has a power output of ten megawatts and operates continuously except for maintenance periods. The apparatus was located in a well shielded area about thirty feet from the core. One series of searches was carried out in the 25-50 MHZ band, and another series of searches in the 4-1000 MHZ band. Small effects were seen but it is not certain whether they are due to transfer from the neutrinos or a correlation effect, or just the result of noise fluctuations. However the power received from the 35-50 MHZ band was less than $10^{-14}$ watts, and for the 4-1000 MHZ experiments the power received was less than $4 \times 10^{-13}$ watts.

The manganese nitrate experiment was repeated at the A.F.R.R.I. Triga Reactor. The pulsed mode was employed, with 1660 megawatt 10 millisecond pulses. The high neutron flux levels and the pulsed mode made observations difficult and it was decided to return to the National Bureau of Standards reactor.

At the National Bureau of Standards reactor there are many experiments which require a constant power level. The reactor is turned off about every forty days for maintenance. The most useful observing times occur when the reactor is being switched on and off. The electron scattering experiments were observing effects too small to be of interest for the major reserach objectives. Extremely long running times would be necessary to verify that the effects were not due to statistical fluctuations. It was decided to explore the neutral current scattering processes, described in detail in Equations D 93-117, enclosed Report.

First a teflon cylinder 0.75 inches in diameter and 2 inches long was employed. The 50 kilowatt reactor at the University of California Irvine was available. The apparatus was approximately 50 feet from the core. The teflon was at room temperature and an increase in temperature was searched for. Results were negative.

The experiment was repeated at the ten megawatt National Bureau of Standards reactor and again results were negative. In these experiments a power output of 3000 ergs per second could have been observed as a heating effect.

It was then decided to employ the $Al^{27}$ nuclei in a sapphire crystal, again 0.75 inches in diameter and 2 inches long. It can be theoretically shown (see Equations 106 and 107 of the enclosed Report) that sapphire should have a much larger total scattering cross section than teflon. Very small effects were suspected at room temperatures. It was then decided to repeat the experiments in a glass Dewar at liquid helium temperatures. Under these conditions a very small heating effect is much easier to observe.

A new series of experiments appears to give a positive result. It is observed that $0.15 \pm 0.03$ ergs per second are generated within the sapphire target as the reactor is switched on.

DISCUSSION

A research reactor area nearly always has a very high level of human and apparatus activity at times when the reactor is being shut down or started. Many important checks are required for the reactor and for continuing experiments near the reactor. Large pumps are switched and large power fluctuations may occur.

Exhaustive checks were carried out to determine if the activity unrelated to the neutrino flux could be causing the observed effects. In addition radiation surveys have been carried out in the vicinity of the sapphire apparatus. The gamma and neutron radiation levels are roughly 0.1 millirems per hour. None of these effects appear capable of producing the 0.15 erg per second heating effect. Therefore it appears possible that the large cross section characteristic of the coherent process of Equations D 93-117 in the enclosed Report is being observed. This conclusion must be regarded as tentative and uncertain, until additional checks can be performed.

Figure 2:
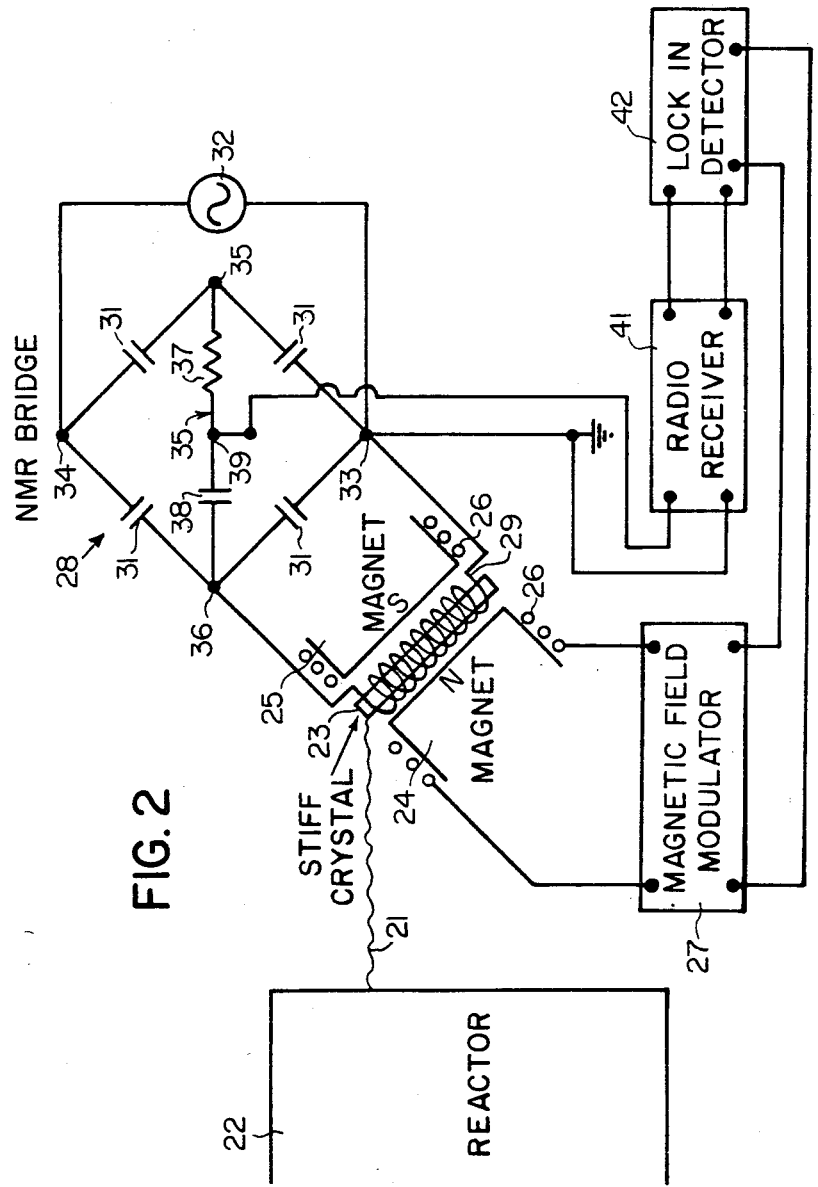
FIG. 2 is a block diagram of a neutrino or photon detector wherein changes, in the precessing angle or spin states of nuclei of a stiff crystal are detected using NMR techniques.

Reference is now made to FIG. 2 of the drawing wherein there is illustrated a second, preferred embodiment of a device for detecting the presence of a neutrino beam 21 derived from a suitable source, such as nuclear reactor 22. Neutrino beam 21 is incident on a bulk material in the form of a very stiff crystal 23, preferably formed of sapphire or silicon and therefore having the isotopes 27Al or 29Si, respectively.

Crystal 23 is located in a DC magnetic field formed in a gap between electromagnets 24 and 25, about which is wound an electromagnet 26 that is periodically activated by a suitable sine wave source, such as a 50 Hz sine wave magnetic field modulator 27. Magnets 24, 25 and 26 are arranged so that the DC magnetic field derived from them is transverse to the longitudinal axis of crystal 23. The intensity of the magnetic field derived from magnets 24, 25 and 26 in the gap between the pole faces of magnets 24 and 25, where crystal 23 is located, is such that there is a tendency for nuclear moments of bulk material 23 to be aligned. Because of the properties of crystal 23, some of the nuclei of the crystal have spin moments different from zero and magnetic moments different from zero. The magnetic field, in aligning the nuclear moments, causes the moments to have an average angle with respect to the field direction. Because of the competing effects of thermal agitation, the alignment of the moments is only partial, so that there is not complete alignment and there is only an average angle which the moments with the field, rather than an absolute angle.

Because crystal 23 is a very stiff piece of bulk material, the nuclei thereof do not recoil alone in response to a neutrino from beam 21 being incident thereon. Instead, in response to a neutrino in beam 21 impinging on crystal 23, the nuclei of the bulk material undergo the same momentum change and do not have independent, random responses. Thereby, the random phase effects normally associated with neutrinos being scattered by bulk matter do not occur. In response to the in-phase scattering of the nuclei of crystal 23, there is a change in the average spin and magnetic moments of the nuclei of crystal 23 relative to the spin state when the nuclei are excited solely by the magnetic fields from magnets 24, 25, 26. The change in scatterer spin state is believed to occur in response to changes in neutrino states in beam 21 in scattering by nuclei of the bulk material in crystal 23.

To detect the change in the nuclear spin states in the magnetic field established by magnets 24, 25 and 26, a nuclear magnetic resonance bridge 28 is provided. Bridge 28 includes a pick-up coil 29, wound about the longitudinal axis of crystal 23 so that the axis of the coil coincides with the longitudinal axis of the crystal. Coil 29 is included as one leg of bridge 28 having capacitors 31 in each of its arms. Bridge 28 is excited by suitable AC source 32, having a frequency typically in the 6 MHz range; source 32 is connected to terminals 33 and 34 of bridge 28. Bridge 28 includes a diagonal 35, connected to terminals 35 and 36, which are orthogonal to terminals 33 and 34. Diagonal 35 includes a series resistor 37 and capacitor 38, between which a tap 39 is provided. The voltage developed between tap 39 and ground, at terminal 33, is coupled to radio receiver 41, tuned to the frequency of source 32. The output of radio receiver 41 is applied to detector 42, which is also responsive to a signal having the same frequency and phase as the signal supplied by modulator 27 to electromagnet 26.

In the embodiment of FIG. 2, the nuclear moments of crystal 23 can be thought of as precessing around the field established by magnets 24, 25 and 26. In response to a single neutrino in beam 21 impinging on crystal 23, the neutrino is scattered, and may thereby be transferring energy/momentum to the nuclei of crystal 23. Because of the stiffness of crystal 23, the crystal recoils as a single entity after absorbing the momentum from each neutrino in beam 21. All nuclei in crystal 23 undergo the same momentum change, thereby providing scattering of the neutrino without random phase effects. The energy change of the neutrino on scattering changes the nuclear spin states as observed by the magnetic resonance apparatus. It is noted that in the apparatus of FIG. 2, there are no emitted radio waves from crystal 23 but that the magnetic fields of the scatterers in crystal 23 are employed for detection. Because there are no emitted radio waves required for detection, the number of steps in the process is reduced and relatively larger effects can be derived to indicate the presence of a neutrino beam.

To establish the required magnetic field intensity for detecting the precessing of the nuclear moments in crystal 23, the magnetic field applied to the crystal while modulator 27 activates electromagnet 26 for successful operation:

$$H = \frac{E_\nu}{4\mu_m \beta \sqrt{2N}}$$

where $E_\nu$ = the energy of a neutrino in beam 21, $\mu_m$ = the scattering nuclear magnetic moment of crystal 23, $\beta^2$ = the fraction of the nuclei of crystal 23 parallel to the magnetic field derived from magnets 24, 25 and 26, and N = the total number of scatterers in crystal 23 for neutrinos in beam 21.

During the time while modulator 27 energizes electromagnet 26, detector 42 is responsive to a signal having an amplitude indicative of the precessing angle of the nuclear moments in crystal 23 as a result of the neutrino beam 21. This amplitude is compared with the amplitude of the signal supplied to detector 42 when crystal 23 is known to be unresponsive to a neutrino beam and while electromagnet 26 is energized by modulator 27. Detector 42 includes conventional circuitry to derive an output indicative of the amplitude of its input while modulator 27 energizes electromagnet 26. As a result of magnetic field applied by the modulator 27, the magnetic field applied to crystal 23 by permanent magnets 24 and 25 modifies the precessing of the magnetic moments and the output of receiver 41 is so modulated, regardless of whether the crystal is responsive to a neutrino beam or not.

As noted supra, crystal 23 must be very stiff so that the nuclei thereof recoil as a single entity after absorbing momentum from beam 21. The crystal 23 is considered to be very stiff if the Debye temperature thereof multiplied by Boltzmann's constant is much greater than (at least an order of magnitude) the square of the neutrino momentum divided by two times the mass of an atom in crystal 23.

Figure 3:
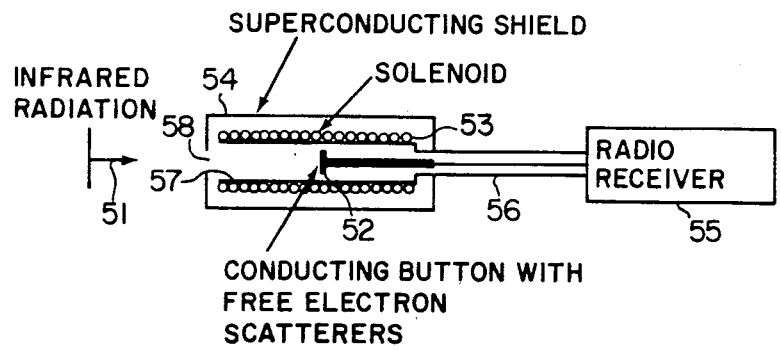

The principles of the invention can also be utilized to detect the presence of optical energy, as illustrated in the embodiment of FIG. 3. Photons instead of neutrinos are incident and are scattered by the magnetic moments of the crystal. Detection is carried out by observing the spin state changes as in the neutrino case. The embodiment of FIG. 3 is suitable to detect optical energy in the infrared region between 1 mm and 100 microns, a spectral region where satisfactory detectors have not been generally available in the past. It is to be understood, however, that the principles described in connection with FIG. 3 are also applicable to higher optical frequencies and shorter wavelengths than 100 microns. The embodiment of FIG. 3 is similar to the previously described embodiments because, in all of the embodiments, coherent scattering of an energy carrying beam occurs, which results in coherent stimulated emission of radiant energy fields in the material. In all of the embodiments, subatomic particles of the material cause the scattering in response to quanta of energy in the beam impinging thereon.

In the embodiment of FIG. 3, an infrared radiation beam 51, in the 1 mm to 100 micron region, is incident on a metal button 52, fabricated preferably of copper, aluminum or some other highly conducting metal with a large quantity of free electrons. Button 52 is arranged so that the face thereof is perpendicular to the axis and propagation direction of beam 51 to intercept the beam. Free electrons on the surface of button 52 coherently scatter photons in beam 51. For each photon in the infrared beam 51 absorbed by a free electron of button 52, the button emits a photon at a much lower frequency, in the microwave region where radio receivers are readily available. The difference between the infrared photon energy absorbed by button 52 and the microwave photon energy emitted from the free electrons of button 52 (reflected in the frequency difference between the absorbed and emitted photons) is absorbed by the ensemble of electrons in button 52, and is reflected as a change in the spin state angle of the electrons with respect to a DC field in which button 52 is located, and which is established by solenoid 53. Solenoid 53 is connected to a suitable DC source and is wound so that the magnetic field derived thereby has a longitudinal axis coincident with the axis of beam 51, and at right angles to the face of button 52. In a manner similar to the embodiment of FIG. 2, electrons of button 52 have magnetic moments with an average angle relative to the magnetic field established by solenoid 53. The average angle is determined by a balance between the magnetic field effects of solenoid 53 and thermal agitation of the electrons. In response to the ensemble of electrons interacting with an infrared photon of beam 51, each electron of button 52 returns to a state sufficiently close to its initial state so that there is no significant random phase shift. The total energy absorbed from the infrared beam is proportional to the square of the number of electrons that scatter beam 51. The magnetic field intensity required to establish the average angle of the electron magnetic moments of the free electrons of button 52 relative to the magnetic field established by solenoid 53 is given by:

$$H = \frac{E_{IR}}{4\mu_e \beta \sqrt{2N}}$$

where $E_{IR}$=the energy of photons in beam 51, $\mu_e$=the magnetic moment of free electrons in button 52, $\beta^2$=the fraction of electrons in button 52 with moments parallel to the magnetic field established by solenoid 53, and N=the number of scattering electrons on the surface of button 52.

For the wavelength region of particular interest, between 1 mm and 100 microns, the magnetic field that must be applied to button 52 is relatively low, less than the ambient, earth magnetic field. Therefore, the magnetic field of the earth must be shielded from button 52 and solenoid 53, a result achieved by surrounding the button and solenoid with a superconducting shield 54, of a known type. If it is desired to detect optical energy having a shorter wavelength, the above equation indicates that the magnetic field intensity must be increased and/or the area of the button irradiated by the optical beam must be decreased. Hence, for shorter wavelength detectors, the need for superconducting shield 54 is obviated.

To detect the shift in the spin quantum states of the electrons in button 52 in response to photons from beam 51, the button is connected to radio receiver 55 via a coax or wave guide conductor. In the illustrated embodiment, button 52 is connected to receiver 55 by coax 56 having a grounded shield 61, and a center conductor that is biased to a negative potential by DC source 62, which is isolated from the r.f. in coax 56 by inductor 63 and capacitor 64. Receiver 55 is tuned to frequencies of the photons emitted from the free electrons of button 52. The frequencies of the electromagnetic waves coupled from button 52 to receiver 55 via line 56 are controlled by the pass band of microwave resonant cavity 57 in which button 52 is located. One end of cavity 57 is effectively formed by button 52, while the other end of the cavity is open. The open end of cavity 57 is in alignment with an aperture 58 in superconducting shield 54. Aperture 58 has a geometry, size and shape that allows beam 51 to pass through it and the opening in cavity 57 whereby the beam impinges on button 52. However, the geometry of aperture 58 is such that it is beyond the cut-off frequency of cavity 57 and the microwave field stored and established in the cavity cannot escape through aperture 51, but is confined to the cavity. The microwave field is coupled by button 52 through transmission medium 56 to receiver 55, which is tuned to the frequencies of cavity 57. Receiver 55 includes conventional circuitry to derive an output indicative of the amplitude of its input. The amplitudes of the inputs to receiver 55 are compared for situations when button 52 is and is not responsive to the optical energy to indicate the presence of the energy.

The infra-red experiments require an applied potential to obtain free electrons. An applied radio frequency field is employed to reduce random phases. Detection is achieved by observing changes in an output radio frequency field by electron spin resonance methods.

FIGS. 4 and 5 are diagrams of apparatus for providing a relatively large number of free electrons for coherent scattering in response to incident optical energy, preferably in the infra-red region between 1 mm and 100 microns. In FIG. 4, conducting button 52 in the apparatus of FIG. 3 is replaced by thin gold film 71, plated on a top face of a dielectric crystal 72, preferably fabricated of a high dielectric material, such as lead zirconate titanate. Film 71 is coated on crystal 72 to a thickness typically less than one wavelength of the optical energy incident on the film and to be detected so the film is substantially transparent to the incident optical energy. The bottom face of crystal 72 is coated by an electrically conducting metal coating 73, preferably silver.

In response to a DC potential being applied to capacitor 74 formed by coating film 71 and 73, as well as dielectric crystal 72, so negative and positive terminals of DC source 72 are respectively applied to film 71 and coating 73, free electrons are concentrated at the interface between film 71 and crystal 72. Because crystal 72 has a very high dielectric constant, usually exceeding one thousand, a large number of free electrons result at the interface for a moderate bias voltage. Alternatively, a higher voltage and lower dielectric crystal can be employed with possible deleterious results. In addition, it is to be understood that gold film 71 can be replaced by any other suitable transparent metal film and that any suitable metal can be employed for coating 73.

Optical radiation transmitted through gold film 71 is coherently scattered by the free electrons in the gold film at the interface between the film and crystal 72. In response to the coherent scattering at the interface between film 71 and crystal 72, coherent radio frequency radiation, having a wavelength typically in the UHF range is derived between film 71 and coating 73 that constitute the electrodes of the capacitor. As illustrated in FIG. 5, the coherent UHF radiation developed between the electrodes of capacitor 74 is coupled by probe 75 into a microwave cavity 76, resonant to the frequency associated with the highest amplitude coherent energy derived from probe 75. The UHF field in cavity 76 is transduced into a UHF electric signal by loop 77 that extends into the cavity through wall 78 that is substantially coplanar with film 71 and is electrically connected to the film. The signal transduced by loop 77 is coupled by coaxial cable 78 to UHF radio receiver 79, tuned to the resonant frequency of cavity 76.

Optical energy to be detected to derived from a suitable source 79, preferably in the wavelength region from 1 mm to 100 microns, and coupled to the interface between film 71 and crystal 72 by a light transmission system including fiber optic rods 81 and 82. Between rods 81 and 82 is located a rotating optical beam chopper 83 that is driven at a suitable frequency to provide chopping of light from source 79 at a relatively low frequency, such as 25 Hertz. To provide synchronous detection for the chopped energy of source 79 that irradiates the interface between film 71 and crystal 72, lock-in detector 84 is driven synchronously by source 85 that also controls the chopping frequency of the light from source 79. Lock-in detector 84 is responsive to a detected DC replica of the RF energy transduced by loop 77, as derived from output terminals of radio receiver 79. Detector 84 thereby provides an indication of the intensity of light from source 79 in the selected wavelength region.

To provide the desired coherent scattering effect achieved by the free electrons at the interface between film 71 and dielectric 72, a DC magnetic field is applied to the free electrons in a direction at right angles to the propagation direction of light from source 79 that is incident on the interface. The DC magnetic field is provided by an electromagnet 85, including pole pieces 86 and 87 of magnetic core 88 on which windings 89 are wound. Windings 89 are energized by a DC source (not shown), whereby a DC magnetic field is established between pole pieces 86 and 87 along the length of the interface between film 71 and crystal 72, at right angles to the propagation direction of light from source 79 that is incident on the interface.

Cavity 76 and the elements therein and thereon, such as film 71, crystal 72, and coating 73, are located in a liquid helium filled dewar 91. Partially immersed within the dewar 91 is cylinder 92, through which fiber optic rod 82 projects. Cylinder 92 has walls made of a non-magnetic material that is also a poor heat conductor, such as stainless steel. Thereby, there is no substantial heat transfer between dewar 91 and the external environment into which cylinder 92 projects, and the magnetic field from electromagnet 86 is coupled to the interface between film 71 and crystal 72. At the bottom of cylinder 92, totally immersed in dewar 91, is cavity 76, having walls made of a highly electrically conductive, non-magnetic material, such as copper. Because cavity 76 is completely immersed in dewar 91, there are no heat transfer problems between the liquid helium in the dewar and the environment outside of the dewar.

Figure 6:
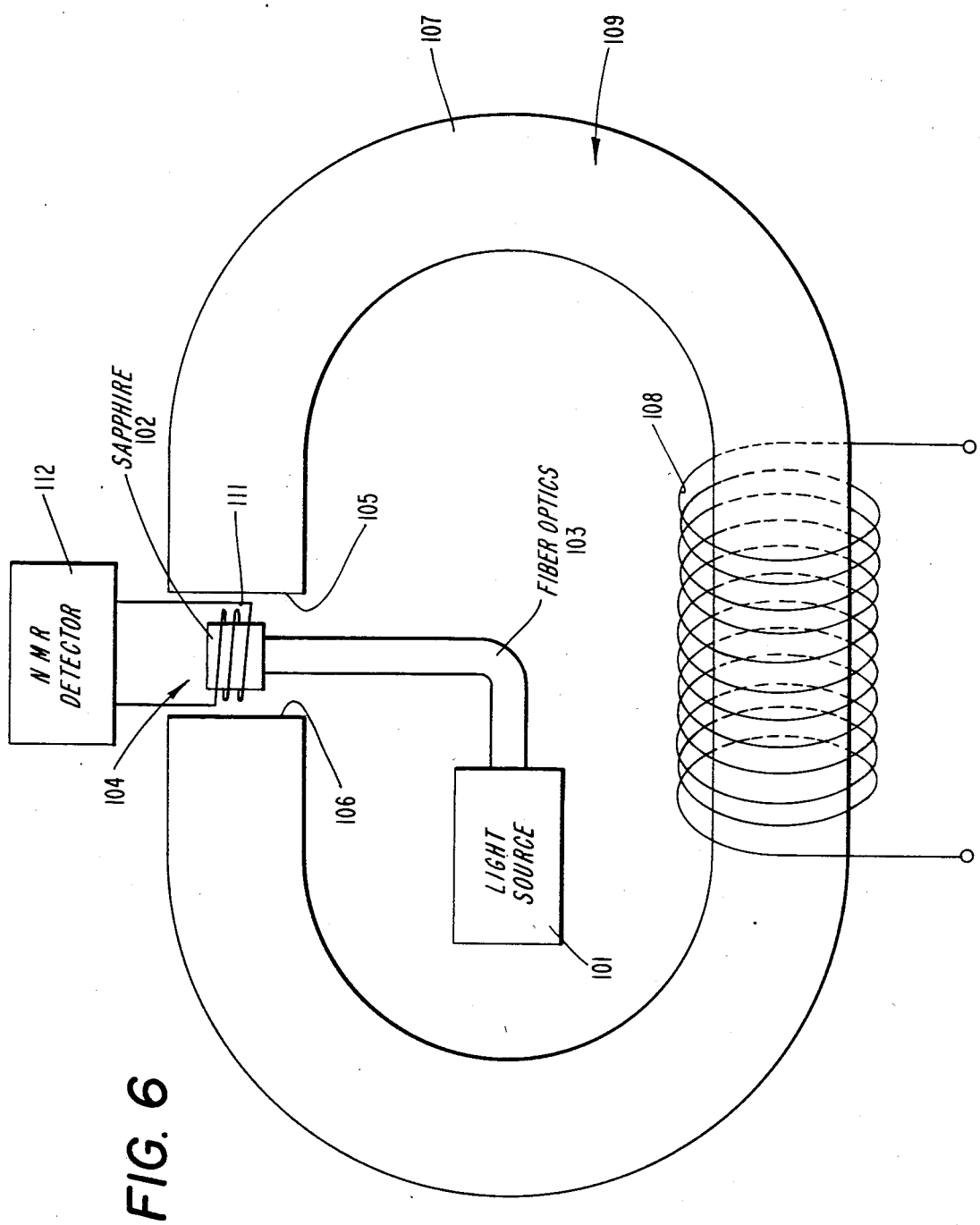
FIG. 6 is a schematic diagram of a further optical energy detector wherein there is coherent interaction between the optical energy and magnetic dipoles in a material.

Reference is now made to FIG. 6 of the drawing wherein there is illustrated a further embodiment of the invention which apparently does not rely directly upon scattering for enabling an energy beam, in particular an optic energy beam, to be detected. In the embodiment of FIG. 6, there is a coherent interaction of the optical beam with aligned dipoles in a material. The interaction changes the magnetic dipole spin state of dipoles aligned in the material by a magnetic field. The magnetic dipole spin state change is detected, preferably by nuclear magnetic resonance detection devices.

In particular, the optical energy from light source 101, preferably having a wavelength in the 1 mm to 100 micron region, is coupled by way of fiber optic rod 103 to slab 102 of a material, preferably a sapphire crystal, having magnetic dipoles. Slab 102 is positioned in air gap 104 between pole pieces 105 and 106 of magnetic core 107, having windings 108 wound thereon. DC current is applied by a suitable source (not shown) to windings 108, to form electromagnet 109 that establishes a DC magnetic field between pole faces 105 and 106, at right angles to the propagation direction of light from source 101 incident on slab 102. The face of slab 102 on which light from fiber optic rod 103 is incident is generally parallel to the magnetic field lines between pole faces 105 and 106.

The magnetic field applied by electromagnet 109 to slab 102 causes magnetic dipoles in the material of the slab to be aligned. While the magnetic field is applied to the material 102, the material is irradiated by the beam from source 101. A coherent interaction occurs between the optical radiation beam and the magnetic dipoles to change the spin of the magnetic dipoles.

To detect the change in spin state of the magnetic dipoles in the material of slab 102, coil 111 is wound about the periphery of slab 102 to detect changes in the nuclear spin quantum states. To this end, coil 111 is wound about the periphery of slab 102 so that the coil has a longitudinal axis extending in the same direction as the propagation direction of optical energy incident on the slab that is transmitted from source 101 and coupled to the slab via fiber optic rod 103. Coil 111 is connected to nuclear magnetic resonance detector 112 which derives an indication of the light from source 101 that is incident on slab 102.

In experiments I have conducted with apparatus similar to that disclosed in FIG. 6, it has been noted that there is considerable absorption by a sapphire crystal of light from a coherent optical source while the sapphire crystal is supplied with a magnetic field from electromagnet 109. I attribute the absorption to a coherent interaction between the beam and magnetic dipoles in the sapphire crystal, whereby a magnetic dipole spin state change occurs.

Neutrino scattering experiments appear most successful when a moderately large nuclear magnetic resonant field is employed. This is believed to be due to the fact that the NMR field removes random phases of scatterer spin ensembles, characteristic of a system in thermal equilibrium. An excessively small NMR field does not produce sufficient spin correlations, while an excessively large NMR produces excessive heating.

While there have been described and illustrated several specific embodiments of the invention, it will be clear that variations in the details of the embodiments specifically illustrated and described may be made without departing from the true spirit and scope of the invention as defined in the appended claims.

What is claimed is:

1. A method of detecting neutrinos comprising the steps of irradiating a material with the neutrinos to cause coherent stimulated emission of radiant energy fields in the material in response to the material being irradiated by the neutrinos, and detecting the coherent radiant energy fields.

2. The method of claim 1 wherein a macroscopically large area of the material interacts with the neutrinos to cause the stimulated emission in response to said area of the material being irradiated by the neutrinos.

3. The method of claim 1 wherein the material is located in a cavity with modes responsive to the coherent radiant energy fields.

4. The method of claim 3 wherein the material is polarized.

5. The method of claim 2 wherein the material is polarized in response to an external polarizing field.

6. The method of claim 2 wherein the energy is electromagnetic.

7. The method of claim 6 wherein the material does not absorb substantial amounts of electromagnetic radiation.

8. The method of claim 7 wherein the material is a dielectric, said dielectric being placed so it is inside of an electromagnetic shield.

9. The method of claim 3 wherein the material is unpolarized, whereby an electromagnetic field having a transverse magnetic or electric field mode is derived in the cavity in response to the neutrino irradiation, and the derived mode is transduced with an electromagnetic field pick-up inside of the cavity.

10. The method of claim 9 wherein the pick-up is positioned to transduce electromagnetic waves propagating in a direction at right angles to the propagation direction of the neutrinos.

11. The method of claim 3 wherein the material includes particles having a spin alignment whereby an electromagnetic field having a transverse electromagnetic mode is derived in the cavity in response to the neutrino irradiation, and the derived mode is detected with an electromagnetic receiver having a pick-up inside of the cavity.

12. The method of claim 11 wherein the pick-up is positioned to transduce electromagnetic waves propagating in a direction at right angles to the propagation direction of the neutrinos.

13. Apparatus for detecting neutrinos comprising a mass of material including electrons or nuclei of atoms that are excited to produce stimulated emission of coherent radiant energy fields in response to the mass being irradiated by the neutrinos, said material being located in a cavity responsive to the coherent fields and being shielded from ambient effects of the fields, a pick-up for the fields in the shielded mass of material for transducing the radiant energy into a coherent output field, and a receiver tuned to the frequencies of the cavity and connected to be responsive to the transduced output fields of the pick-up.

14. The apparatus of claim 13 wherein the cavity is resonant to a frequency of the transduced output fields and is a shield for the ambient effects.

15. The apparatus of claim 14 wherein the material is a dielectric, and electromagnetic fields are produced in response to electrons or nuclei of the material returning to a state after having been pumped by the neutrinos, whereby the energy is electromagnetic.

16. The apparatus of claim 15 wherein the pick-up is positioned to be responsive to an electromagnetic wave propagating in a direction at right angles to the direction of neutrino propagation.

17. The apparatus of claim 15 wherein the material is paramagnetic, and means for applying a polarizing magnetic field to the material.

18. The apparatus of claim 17 further including means for modulating the magnetic field and means for synchronously detecting the coherent output waves alternately derived from the pick-up.

19. The apparatus of claim 15 wherein the material is unpolarized whereby an electromagnetic field is excited in the cavity, said pick-up being oriented to be responsive to a derived mode of the electromagnetic field.

20. A method of detecting an energy beam, the energy beam consisting of an optical or neutrino beam having a frequency range, comprising the steps of irradiating a material with the beam, said material interacting with the beam to cause coherent scattering of the beam, the coherent scattering of the beam causing coherent emission of radiant energy fields in the material, the radiant energy fields having a frequency lower than the frequency range of the beam, and detecting the coherent radiant energy fields.

21. The method of claim 20 wherein the material has a macroscopically large area interacting with the beam and has nuclei having sufficient stiffness so that the nuclei recoil as a single entity after absorbing momentum from the beam.

22. The method of claim 21 wherein the material is a stiff crystal such that $$p^2/2m << k \times \theta_D$$

where
p = momentum of quantums of energy in the beam,
m = mass of an atom of the crystal,
k = Boltzmann's constant ($1.38 \times 10^{-23}$ joules/degree C.), and
$\theta_D$ = Debye temperature of the crystal.

23. The method of claim 20 wherein a macroscopically large area of the material interacts with the energy beam to cause the stimulated emission in response to said area of the material being irradiated by the energy beam.

24. The method of claim 20 wherein a macroscopically large area of the material interacts with the energy beam to cause subatomic particles in said area to be coherently scattered in response to the interaction between the quanta of energy in the beam to cause the coherent emission of the radiant energy fields in said area of the material.

25. The method of claim 20 wherein the beam is a neutrino beam.

26. The method of claim 25 wherein the material is a bulk material having nuclei with non-zero spin and non-zero magnetic moments and sufficient stiffness to recoil as a single entity after absorbing momentum from each neutrino in the beam, applying a magnetic field to the material while it is irradiated by the beam, said magnetic field causing the nuclei to normally precess about the magnetic field at a predetermined average angle, said beam causing a shift in the occurrence of the processing angle, said detecting the precessing angle shift.

27. The method of claim 26 wherein the magnetic field intensity is substantially equal to $$H = \frac{E_\nu}{4\mu_m \beta \sqrt{2N}}$$

where
$E_\nu$ = the energy of neutrinos in the beam,
$\mu_m$ = the scattering nuclear magnetic moment of the material,
$\beta^2$ = fraction of nuclei of the material with moments parallel to the direction of the magnetic field, and
N = the total number of neutrino scatters of the material.

28. The method of claim 27 wherein the shift of the precessing angle is detected with nuclear magnetic resonance detecting apparatus.

29. The method of claim 26 wherein the material is a stiff crystal such that $$p^2/2m << k \times \theta_D$$

where
p = neutrino momentum
m = mass of an atom of the crystal
k = Boltzmann's constant ($1.38 \times 10^{-23}$ joules/degree C.), and
$\theta_D$ = Debye temperature of the crystal.

30. The method of claim 29 wherein the crystal is sapphire.

31. The method of claim 29 wherein the crystal is selected from the group consisting of Lithium Niobate or Lithium Fluoride Silicon.

32. The method of claim 20 wherein the material has subatomic particles with non-zero spin and non-zero magnetic moments and sufficient stiffness to recoil as a single entity after absorbing momentum from each quantum of energy in the beam, applying a magnetic field to the material while it is irradiated by the beam, said magnetic field causing the subatomic particles to normally precess about the magnetic field at a predetermined average angle, said beam causing a shift in the precessing angles, and detecting the occurrence of the precessing angle shift.

33. The method of claim 32 wherein the magnetic field intensity is substantially equal to $$H = \frac{E_\nu}{4\mu_m \beta \sqrt{2N}}$$

where
- $E_\nu$ = the energy of quantums of energy in the beam,
- $\mu_m$ = the scattering nuclear magnetic moment of the material,
- $\beta^2$ = fraction of nuclei of the material with moments parallel to the direction of the magnetic field, and
- N = the total number of scatters of the material for the quanta of energy in the beam.

34. The method of claim 32 wherein the material is a stiff crystal such that $$p^2/2m \ll k \times \theta_D$$

where
- p = momentum of quantums of energy in the beam,
- m = mass of an atom of the crystal,
- k = Boltzmann's constant ($1.38 \times 10^{-23}$ joules/degree C.), and
- $\theta_D$ = Debye temperature of the crystal.

35. The method of claim 20 wherein the material has subatomic particles with non-zero spin and non-zero magnetic moments, applying a magnetic field to the material while it is irradiated by the beam, said magnetic field causing the particles to normally precess about the magnetic field at a predetermined average angle, said beam causing a shift in the precessing angle so that the coherent stimulated emission of the radiant energy fields occurs in response to the interaction between the quantum of energy in the beam and the change in the precessing of the subatomic particles, and detecting the occurrence of the precessing angle shift.

36. The method of claim 20 wherein the beam is a optical energy beam.

37. The method of claim 36 wherein the material includes free electrons that coherently scatter photons of the optical energy beam to derive a coherent ensemble of photons having a frequency much lower than the frequency of the optical energy, applying a magnetic field to the material while it is irradiated by the beam, said magnetic field causing the electrons to normally precess about the magnetic field at a predetermined angle, said beam causing a shift in the precessing angle, and detecting the occurrence of the precessing angle shift.

38. The method of claim 37 wherein the magnetic field intensity is substantially equal to $$H = \frac{E_{IR}}{4\mu_e \beta \sqrt{2N}}$$

where
- $E_{IR}$ = photon energy of the optical beam,
- $\mu_e$ = electron magnetic moment of the material,
- $\beta^2$ = fraction of electrons with moments parallel to the magnetic field direction, and
- N = number of scattering electrons in the material.

39. The method of claim 37 wherein the precessing angle shift is detected by detecting the coherent ensemble of photons with a radio receiver tuned to the much lower frequency.

40. The method of claim 37 or 38 further including shielding the material and the magnetic field applied to the material from ambient magnetic fields.

41. The method of claim 38 or 40 wherein the precessing angle shift is detected by detecting the coherent ensemble of photons with a radio receiver tuned to the much lower frequency.

42. Apparatus for detecting an energy beam, the energy beam consisting of an optical or neutrino beam in a frequency range, comprising a mass of material positioned to intercept the beam, means for supplying an energy field to said mass of material to cause subatomic particles of the material to be coherently scattered in response to an interaction between quanta of energy in the beam and the particles, the coherent scattering of said subatomic particles causing coherent emission of radiant energy fields in the material, the radiant energy fields having a frequency lower than the frequency range of the beam, and means responsive to the radiant energy fields for detecting the occurrence of said fields.

43. The apparatus of claim 42 wherein the beam is a neutrino beam and the material is a bulk material having nuclei with non-zero spin and non-zero magnetic moments and sufficient stiffness to recoil as a single entity after absorbing momentum from each neutrino in the beam, said energy field supplying means including means for applying a magnetic field to the material while it is irradiated by the beam, said magnetic field causing the nuclei to normally precess about the magnetic field at a predetermined average angle, said beam causing a shift in the precessing angle, said means for detecting the occurrence of the precessing angle shift.

44. The apparatus of claim 43 wherein the magnetic field intensity as substantially equal to $$H = \frac{E_\nu}{4\mu_m \beta \sqrt{2N}}$$

where
- $E_\nu$ = the energy of neutrinos in the beam,
- $\mu_m$ = the scattering nuclear magnetic moment of the material,
- $\beta^2$ = the fraction of nuclei of the material with moments parallel to the direction of the magnetic field, and
- N = the total number of neutrino scatters of the material.

45. The apparatus of claim 42 wherein the material is a sapphire crystal.

46. The apparatus of claim 42 wherein the material is a silicon crystal.

47. The apparatus of claim 42 wherein the material is a lithium niobate crystal.

48. The apparatus of claim 44 wherein the means for detecting includes nuclear magnetic resonance detecting means and means for adjusting the NMR radio frequency field to enhance the coherent scattering by producing correlated spin states.

49. The apparatus of claim 42 wherein the material has subatomic particles with non-zero spin and non-zero magnetic moments, said energy field supplying means including means for applying a magnetic field to the material while it is irradiated by the beam, said magnetic field causing the subatomic particles to normally precess about the magnetic field at a predetermined average angle, said beam causing a shift in the precessing angle, and means for detecting the occurrence of the precessing angle shift.

50. The apparatus of claim 42 wherein the beam is an optical energy beam and the material includes free electrons that coherently scatter photons of the optical energy beam to derive a coherent ensemble of photons having a frequency much lower than the frequency of the optical energy, said energy field supplying means including means for applying a magnetic field to the material while it is irradiated by the beam, said magnetic field causing the nuclei to normally precess about the magnetic field at a predetermined angle, said beam causing a shift in the occurrence of the precessing angle, and means for detecting the precessing angle shift.

51. The apparatus of claim 50 wherein the photons at the much lower frequency establish an RF field at the much lower frequency, said material being a metal button irradiated by the beam, means coupled to the button for storing the RF field, means for coupling the RF field in the storing means to a radio receiver, means for providing a potential to control the number of free electrons and for providing an external electron spin resonance field to correlate the spin states, the means for detection including means for detecting electron spin resonance.

52. The apparatus of claim 50 wherein the means for storing includes a resonator tuned to a frequency of the RF field, said button being located in the resonator, said resonator including an aperture for enabling the beam to impinge on the button, said aperture having a geometry such that it is beyond cut-off for the RF field so that the RF field cannot escape from the resonator through the aperture.

53. The apparatus of claim 52 further including means for shielding the resonator, button and magnetic field applying means for ambient magnetic fields.

54. The apparatus of claim 53 wherein the means for shielding includes a superconducting coil.

55. The method of claim 20 wherein the material has subatomic particles with non-zero spin and non-zero magnetic moments and sufficient stiffness to recoil as a single entity after absorbing momentum from each quantum of energy in the beam, applying a magnetic field to the material while it is irradiated by the beam, said magnetic field causing the subatomic particles to normally precess about the magnetic field at a predetermined average angle, said beam causing a shift in the quantum states of the scatterers, and detecting the change in quantum states by nuclear magnetic resonance apparatus.

56. The method of claim 25 wherein the material is a bulk material having nuclei with non-zero spin and non-zero magnetic moments and sufficient stiffness to recoil as a single entity after absorbing momentum from each neutrino in the beam, applying a magnetic field to the material while it is irradiated by the beam, said magnetic field causing the nuclei to normally precess about the magnetic field at a predetermined average angle, said beam changing the quantum state of the scatterers, and detecting the change in quantum state by nuclear magnetic resonance techniques.

57. The method of claim 20 wherein the beam is a photon beam.

58. The method of claim 29 wherein the crystal is selected from the group consisting of Lithium Niobate or Lithium Fluoride.

59. The apparatus of claim 41 wherein the beam is an optical energy beam and the material includes free electrons that coherently scatter photons of the optical energy beam to derive a coherent assemble of photons having a frequency much lower than the frequency of the optical energy, said material being an electrode of a capacitor having a dielectric, the capacitor having an interface between the electrode and the dielectric, the electrode being transparent to the optical energy so that photons from the beam incident on the interface are scattered by the free electrons at the interface.

60. The apparatus of claim 59 wherein the detecting means includes a resonant cavity responsive to a frequency of the coherent emission.

61. The apparatus of claim 42 or 43 wherein the detecting means includes a nuclear magnetic resonant detector.

62. The method of claim 59 wherein the electrode is a thin gold film for producing a relatively large number of free electrons.

63. The method of claim 59 or 62 further including means for biasing the capacitor to supply the free electrons at the interface.

64. A method of detecting an energy beam, the energy beam consisting of an optical or neutrino beam, comprising the steps of irradiating a material having magnetic dipoles with the beam, applying a magnetic field to the material while the material is irradiated by the beam, the magnetic field aligning magnetic dipoles in the material, a coherent interaction occurring between the beam and the aligned magnetic dipoles to change the magnetic dipole spin state, and detecting the magnetic dipole spin state.

65. The method of claim 64 wherein the beam is an optical energy beam.

66. The method of claim 64 or 65 wherein the magnetic dipole spin state is detected with a nuclear magnetic resonance detector.

67. The method of claim 64 or 65 wherein components of the magnetic field and the propagation direction beam incident on the material are at right angles to each other.

68. Apparatus for detecting an energy beam, the energy beam consisting of an optical or a neutrino beam, comprising a mass of material having magnetic dipoles positioned to intercept the beam, means for supplying a magnetic field to said mass of material to align the dipoles, a coherent interaction of the beam with the aligned dipoles occurring to change the magnetic dipole spin state, and means for detecting the magnetic dipole spin state change.

69. The apparatus of claim 68 wherein the means for detecting includes a coil inductively coupled to the material for deriving an electric signal in response to the spin state change, and a nuclear magnetic resonant detector responsive to the electric signal.

* * * * *